United States Patent [19]
Tanaka et al.

[11] Patent Number: 5,132,450
[45] Date of Patent: Jul. 21, 1992

[54] PROCESS FOR PRODUCING HIGH PURITY ISOPHTHALIC ACID

[75] Inventors: Kazuo Tanaka; Terumasa Yoshida; Fumio Okoshi; Ichihei Motoyama, all of Kurashiki; Tazuo Ohta, Tokyo; Toshiaki Abe, Yokohama, all of Japan

[73] Assignee: Mitsubishi Gas Chemical Company, Inc., Tokyo, Japan

[21] Appl. No.: 722,555

[22] Filed: Jun. 25, 1991

[30] Foreign Application Priority Data

Jun. 25, 1990 [JP] Japan .................. 2-164217
Apr. 23, 1991 [JP] Japan .................. 3-117896

[51] Int. Cl.$^5$ ................ C07C 51/265; C07C 51/42; C07C 51/44
[52] U.S. Cl. .................. 562/414; 562/413; 562/416; 562/417; 562/485; 562/608
[58] Field of Search ............... 562/413, 414, 485, 608

[56] References Cited

U.S. PATENT DOCUMENTS

| | | | |
|---|---|---|---|
| 3,859,344 | 1/1975 | Shigeyasu et al. | 562/413 X |
| 4,051,178 | 9/1977 | Kimura et al. | 562/414 |
| 4,053,506 | 10/1977 | Park et al. | 562/414 |
| 4,197,412 | 4/1980 | Kimura et al. | 562/416 |
| 4,769,487 | 9/1988 | Hundley et al. | 562/413 |
| 4,772,748 | 9/1988 | Hashizume et al. | 562/413 |
| 4,855,491 | 8/1989 | Chew et al. | 562/414 |
| 4,855,492 | 8/1989 | Hundley | 562/414 |

FOREIGN PATENT DOCUMENTS

| | | |
|---|---|---|
| 0021747 | 1/1981 | European Pat. Off. |
| 1555246 | 11/1979 | United Kingdom |
| 1577019 | 10/1980 | United Kingdom |

Primary Examiner—Jose G. Dees
Assistant Examiner—Vera C. Clarke
Attorney, Agent, or Firm—Wenderoth, Lind & Ponack

[57] ABSTRACT

A process for producing isophthalic acid by oxidation of m-xylene with an oxygen-containing gas in a hydrous acetic acid solvent in the presence of a cobalt/manganese/bromine system catalyst, the process being capable of industrially advantageously producing high-purity isophthalic acid having excellent whiteness, the process comprising (1) a step of carrying out an oxidation reaction in a main oxidation reactor under specified ranges of a catalyst concentration, a reaction temperature and an oxygen concentration in a discharge gas such that the concentration of 3-carboxybenzaldehyde becomes 500 to 10,000 ppm, (2) a step of further carrying out an oxidation reaction in a post oxidation reactor such that the concentration of 3-carboxybenzaldehyde becomes 100 to 800 ppm, separating crude isophthalic acid, evaporating remaining mother liquor and recovering acetic acid, and (3) mixing the crude isophthalic acid with purified acetic acid, stirring the resultant mixture at 100° C. or higher, and separating purified isophthalic acid.

19 Claims, No Drawings

PROCESS FOR PRODUCING HIGH PURITY ISOPHTHALIC ACID

FIELD OF THE INVENTION

The present invention relates to a process for producing isophthalic acid by liquid phase oxidation of m-xylene. High purity isophthalic acid is useful as an intermediate material for polymers such as an unsaturated polyester resin, an alkyd resin, a modified polyester fiber, heat-resistant polyamide, etc.

PRIOR ART OF THE INVENTION

As a process for producing an aromatic carboxylic acid, there is known a process in which an aromatic hydrocarbon having an aliphatic substituent is subjected to liquid phase oxidation with molecular oxygen in a solvent of an aliphatic carboxylic acid such as acetic acid, etc., in the presence of a catalyst comprising a heavy metal and bromine. This process can be applied to the production of isophthalic acid.

British Patent 1555246 specifically discloses a process for oxidizing m-xylene with air in an acetic acid solvent in the presence of a catalyst comprising cobalt, manganese and bromine, and this process has been widely industrially practiced. Since, however, the isophthalic acid produced by this process contains a large amount of impurities including 3-carboxybenzaldehyde (to be sometimes referred to as 3CBA hereinafter), a polymer directly produced from this isophthalic acid as a material has no excellent hue, nor is it suitable for high-function use. In particular, with an advance in industrial technology in recent years, requirements of qualities of polyester products as a highly functional material are increasingly severe, and therefore, isophthalic acid as a material for polyester is desired to have high purity and excellent whiteness.

In order to highly purify crude isophthalic acid produced by oxidation, a method disclosed in British Patents 1,152,575 and 1,152,576 can be employed in which an aqueous solution of a crude isophthalic acid is subjected to hydrogenation and purification at a high temperature in the presence of a palladium catalyst.

On the other hand, terephthalic acid is produced by oxidizing p-xylene in the same manner as in the production of m-xylene, and it is general practice to employ a process in which a high-purity terephthalic acid is directly produced without carrying out the above hydrogenation, purification, etc. That is, Japanese Patent Publication No. 36732/1970 discloses a process for producing terephthalic acid usable for direct polymerization, which comprises oxidizing p-xylene in the presence of a cobalt/manganese/bromine system catalyst mainly comprising cobalt and containing 1 to 20% by weight, based on the cobalt, of manganese. This process uses a large amount of expensive cobalt. Therefore, many processes for producing high-purity terephthalic acid have been proposed in which the catalyst amount and the acetic acid combustion amount are decreased by improvements in the oxidation conditions and oxidation method (U.S. Pat. No. 4,160,108, U.S. Pat. No. 4,053,506, British Patents 1,511,181 and 1,511,182, U.S. Pat. No. 4,051,178, U.S. Pat. No. 4,197,412, British Patent 1,454,478, Bristish Patent 1,577,019 and U.S. Pat. No. 3,859,344).

The conventional process for purifying crude isophthalic acid by hydrogenation in the presence of a palladium catalyst requires separate apparatus for a hydrogenation reaction, crystallization, etc., and a high investment for apparatus for purification and much labor is required, which causes an increase in the production cost.

The present inventors attempted to apply the above process for producing high-purity terephthalic acid by oxidation of p-xylene to a process for producing isophthalic acid by oxidation of m-xylene. As a result, it has been found that the conventional process for producing terephthalic acid cannot be directly applied to the process for producing isophthalic acid due to the following problems.

(1) Even in the oxidation of m-xylene, intermediates such as m-toluic acid and 3CBA can be almost fully removed by carrying out post oxidation after a main oxidation reaction as is described in U.S. Pat. No. 3,859,344. However, if the amount of 3CBA is decreased to become smaller than a certain amount, no isophthalic acid having excellent whiteness can be obtained, and the amount of coloring impurities, on the contrary, increases to deteriorate the quality of isophthalic acid.

(2) When acetic acid is recovered by evaporation of a reaction liquid from which isophthalic acid has been separated (i.e. mother liquor), the recovery of acetic acid is poor and the loss of acetic acid is large. The reason therefor is that the solubility of isophthalic acid in acetic acid around the boiling point of acetic acid is about 10 times higher than that of terephthalic acid, and the mother liquor obtained after separation of isophthalic acid crystals contains a larger amount of dissolved isophthalic acid. When the recovery of acetic acid is increased, a high-boiling substance in the state of a high-temperature melt, i.e. a residue in an evaporator, shows a decrease in fluidity, and the operationability of the evaporator is deteriorated extremely. In particular, therefore, such an evaporator as a film evaporator cannot be suitably used.

SUMMARY OF THE INVENTION

It is an object of the present invention to provide a process for producing isophthalic acid having both high purity and excellent whiteness.

It is another object of the present invention to provide a process for producing isophthalic acid having both high purity and excellent whiteness at high yields.

It is further another object of the present invention to provide an industrially advantageous process for producing isophthalic acid having both high purity and excellent whiteness with simple apparatus, which process also permits high recovery of acetic acid.

Further, it is another object of the present invention to provide a process for producing isophthalic acid having high purity and excellent whiteness at high yields in the presence of an inexpensive catalyst.

According to the present invention, there is provided a process for producing high-purity isophthalic acid by oxidizing m-xylene with an oxygen-containing gas in a solvent of hydrous acetic acid in the presence of a cobalt/manganese/bromine system catalyst, the process comprising:

a first step of feeding an oxidation reactor with the solvent, m-xylene of which the amount is 1 to 1/15 times the weight of the solvent and the catalyst in which the total amount of cobalt and manganese is in the range between 300 ppm and 1,500 ppm based on the weight of the solvent, the atomic ratio of manganese to cobalt (manganese/cobalt) is 0.5 to 5 and the atomic ratio of bromine to the total amount of cobalt and manganese (bromine/total of cobalt and manganese) is 0.5 to 1.5, and carrying out oxidation of m-xylene at a temperature between 180° C. and 210° C. with maintaining 2 to 8% by volume of an oxygen concentration in a discharge gas until crude isophthalic acid produced in this first step has a 3-carboxybenzaldehyde concentration in the range between 500 ppm and 10,000 ppm and the total amount of isophthalic acid and intermediates produced by the oxidation is 10 to 35% by weight based on the weight of the solvent, b. a second step of further oxidizing a mixture formed by the oxidation in the first step until the crude isophthalic acid has a 3-carboxybenzaldehyde concentration in the range between 100 ppm and 800 ppm, separating the crude isophthalic acid, evaporating remaining mother liquor to obtain a condensate, and purifying the condensate by distillation to recover acetic acid, and c. a third step of mixing the crude isophthalic acid separated in the second step with purified acetic acid, treating the resultant mixture by stirring it at a temperature of not less than 100° C., and separating purified isophthalic acid.

DETAILED DESCRIPTION OF THE INVENTION

Having focussed on characteristics of the oxidation of m-xylene, the present inventors have further made a diligent study of the application of the above process for producing high-purity terephthalic acid, and as a result, found the following. Main oxidation and post oxidation are separately carried out in the presence of a specific amount of a hydrous acetic acid solvent and a catalyst up to predetermined limits of oxidation. and specific purification treatment is carried out, whereby (1) high-purity isophthalic acid having excellent whiteness can be obtained, (2) acetic acid can be effectively recovered from mother liquid from which isophthalic acid crystals have been separated, and can be recycled, and (3) the combustion amount of acetic acid in a reactor can be decreased. The present invention has been completed on this finding.

In the process of the present invention, in a first step, m-xylene is oxidized with an oxygen-containing gas in a hydrous acetic acid solvent in the presence of a catalyst comprising a cobalt compound, a manganese compound and a bromine compound.

As a starting material, m-xylene is generally used. However, substituents on the benzene ring are not limited to methyl groups, and may be ethyl, propyl or isopropyl groups, or a combination of these. Further, the substituent may be a group which can be oxidized to a carboxyl group. One of the two substituents may also be a carboxyl group.

m-Xylene is fed to an oxidation reactor continuously in this step, the feed rate of m-xylene per liter of the solvent volume retained in the reactor is 0.05 to 0.2 kg/hour, and the reaction time is 10 to 120 minutes, preferably 20 to 90 minutes.

Hydrous acetic acid is used as a solvent for the reaction. The hydrous acetic acid to be fed to the oxidation reactor has a water concentration of 3 to 15% by weight, preferably 5 to 12% by weight. When the water concentration is too low, the resultant isophthalic acid is liable to be deteriorated in color quality, and the combustion amount of acetic acid increases. When the water concentration is too high, the oxidation activity in the reaction decreases, the reaction takes longer, and the resultant isophthalic acid shows degradation in quality.

Hydrous acetic acid as a solvent is used in such an amount that the total amount of isophthalic acid and intermediates (m-toluic acid and 3CBA) produced by the oxidation in the oxidation reactor is 10 to 35% by weight. In this case, in general, the feed amount of the solvent is 1 to 15 times, preferably 3 to 12 times the weight of m-xylene. When the total amount of the isophthalic acid and intermediates is less than 10% by weight in concentration, the amount of the solvent is relatively large. Unexonomically, therefore, a large-sized apparatus for separation of crystals is required, and the amount of the solvent to be treated in a solvent recovery step is large. When the above total amount is more than 35% by weight in concentration, a tube from a post oxidation reactor to a crystallizer of crude isophthalic acid and the crystallizer are liable to be clogged.

The cobalt compound, manganese compound and bromine compound are selected from known compounds used for liquid phase oxidation, such as carbonates, acetic acid salt tetrahydrates, bromides, etc., of cobalt and manganese. As a bromine compound, preferred is an inorganic compound which is dissolved in the solvent and readily dissociated to form ions. Particularly preferred are hydrobromic acid, cobalt bromide, manganese bromide, etc.

In a catalyst metal concentration, the total amount of cobalt and manganese based on the solvent weight is in the range of 300 ppm and 1,500 ppm, preferably between 400 ppm and 1,200 ppm, and the atomic ratio of manganese to cobalt is 0.5 to 5, preferably 0.8 to 4. Bromine is used in such a concentration that the atomic ratio of bromine to the total amount of cobalt and manganese is 0.5 to 1.5, preferably 0.6 to 1.2. When these metal components are used in the above ranges, the 3CBA concentration is suitably retained through the main oxidation and the post oxidation, an isophthalic acid having excellent hue is obtained, and the combustion amount of acetic acid is remarkably small.

The reaction temperature in the first step is in the range between 180° C. and 210° C., and the pressure is set at a level sufficient to maintain a liquid phase of the solvent. In general, the reaction is carried out at a pressure between 10 kg/cm$^2$ and 25 kg/cm$^2$.

As an oxygen-containing gas, air is generally used. Air is fed into the reaction liquid such that the discharge gas from the oxidation reactor has an oxygen concentration of 2 to 8% by volume, preferably 3 to 6% by volume.

In the main oxidation in the first step, the operational factors such as the residence time, the reaction temperature, etc., are controlled such that crude isophthalic acid produced under the conditions in the above ranges has a 3CBA concentration in the range between 500 ppm and 10,000 ppm. When the 3CBA concentration is too low at this stage, the oxidation degree is too high. As a result, the amount of coloring impurities increases, and even the post oxidation produces no effect. Therefore, the resultant isophthalic acid shows no improvement in color quality. Further, this means that the combustion amount of acetic acid increases, which is very disadvantageous economically. When the 3CBA concentration is higher than the above upper limit, 3CBA is not sufficiently oxidized in the post oxidation, and no high-purity isophthalic acid is obtained.

The above 3CBA concentration is determined by measuring crude isophthalic acid crystals obtained by taking out an oxidation reaction mixture from a reactor used in the first step and subjecting it to solid-liquid separation.

In the second step, at first, a mixture of oxidation reaction products produced in the first step is post-oxidized with an oxygen-containing gas. In general, in the case of a continuous method, this post oxidation is carried out in a crystallizer vessel into which the above mixture has been recharged. The post oxidation may be also carried out during the step when the mixture is cooled after the main reaction in the first step. The post oxidation reaction is carried out at a temperature between the main oxidation reaction temperature in the first step and a temperature which is lower than the main oxidation reaction temperature by about 30° C. It is industrially disadvantageous to set the temperature for the post oxidation reaction at a level higher than that for the main oxidation reaction, since heating is required. Moreover, such a higher temperature the post oxidation is liable to cause degradation in color quality. When the post oxidation reaction temperature is too low, the post oxidation is insufficient, and no high-purity isophthalic acid is obtained.

As an oxygen-containing gas for the post oxidation, air can be used. A discharge gas from the oxidation in the first step may be used. The oxygen concentration in a discharge gas in the second step is maintained so as to be 2 to 7% by volume.

The post oxidation is carried out for such a period of time that an intended oxidation substantially proceeds, i.e. for 1 to 300 minutes, preferably for 2 to 120 minutes.

The most important point in the second step is that the oxidation reaction liquid obtained by the post oxidation has a 3CBA concentration in the crude isophthalic acid in the range between 100 ppm to 800 ppm. The reasons therefore are as follows.

(1) The reaction mixture obtained by the post oxidation is cooled to crystallize isophthalic acid, crystals of isophthalic acid are separated from a liquid of the reaction mixture, and the crystals are purified in the next third step. When the crude isophthalic acid has a 3CBA concentration in the above range, a high-purity isophthalic acid having excellent whiteness can be obtained.

In addition, when the crude isophthalic acid obtained by the post oxidation has a 3CBA concentration of higher than 800 ppm, no high-purity isophthalic acid is obtained even after the purification is carried out in the third step. When the 3CBA concentration is lower than 100 ppm, no purified isophthalic acid having excellent whiteness is obtained.

(2) Mother liquor remaining after the separation of isophthalic acid from the oxidation reaction liquid contains high-boiling substances such as a coloring substance, etc., in addition to acetic acid, water, a catalyst composition, benzoic acid, m-toluic acid, 3CBA, isophthalic acid, phthalic acid and trimellitic acid. A detailed study by the present inventors has shown that the fluidity of a mother liquor residue in an evaporator at a high temperature after the isophthalic acid has been separated greatly depends upon content of acetic acid, water, a catalyst composition, benzoic acid, 3CBA, m-toluic acid, trimellitic acid, etc., relative to the content of isophthalic acid.

That is, when the 3CBA in the post oxidation reaction liquid is lower than the above lower limit, the fluidity of the mother liquor residue in an evaporator at a high temperature is greatly reduced due to a change in the composition of the residue, and acetic acid therefore cannot be effectively evaporated. When the 3CBA concentration is in the above range, acetic acid can be effectively recovered.

The oxidation reaction liquid obtained by the post oxidation is recharged into a crystallizer, and cooled to a temperature between about 110° C. and about 80° C. to finally precipitate isophthalic acid crystals. Then, the crystals are recovered by filtering, and subjected to the third step. The filtrate mother liquor is evaporated to separate high-boiling substances in the state of a melt, and a condensate of recovered vapor is purified by distillation to recover purified acetic acid. For this evaporation, a film evaporator can be suitably used. The mother liquor may be recycled to the oxidation reactor in the first step, and in this case, a remaining portion of the mother liquor is evaporated as above, and the above purification by distillation is carried out to recover acetic acid.

When a film evaporator is used, it is preferred to distill the mother liquor partially or wholly with a distillation column before the evaporation in order to reduce the load of the mother liquor on the film evaporator, and a column bottom liquid is evaporated with the film evaporator. As a film evaporator, a film evaporator of a type supplied by Luwa is suitably usable in the present invention, and the temperature of the condensate is adjusted to a temperature between 130° C. and 230° C. It is preferred to further rectify an acetic acid aqueous solution separated from the distillation column and acetic acid from the film evaporator, and formed water is separated by this rectification. Acetic acid recovered can be used as a solvent in the first step or as a wash liquid in the third step.

In the third step, isophthalic acid crystals recovered from the reaction mixture in the second step are suspended in purified acetic acid, and the resultant suspension is stirred at a temperature of about 100° C. or higher. Thereafter, isophthalic acid crystals are separated. For this stirring, a retention temperature of about 100° C. or higher is sufficient, and it is not necessary to increase the retention temperature so as to dissolve isophthalic acid completely. The retention time is 10 to 60 minutes. In the present invention, the "purified acetic acid" refers to acetic acid which substantially does not contain impurities.

The isophthalic acid crystals separated above are washed with purified acetic acid. In this case, acetic acid recovered in the second step or industrial acetic acid may be used. The acetic acid for washing the above isophthalic acid crystals may be hydrous acetic acid. The amount of purified acetic acid for use is 1 to 5 times the weight of the isophthalic acid crystals. After the washing, the isophthalic acid crystals are dried, whereby purified isophthalic acid having excellent whiteness can be obtained.

Mother liquor remaining after the isophthalic acid crystals have been separated in the third step can be used as a solvent for the liquid phase oxidation in any of the first and second step. Due to this, isophthalic acid dissolved in the mother liquor is recovered in the oxidation step.

According to the present invention, high-purity isophthalic acid having excellent color quality useful as a polymer material for an unsaturated polyester resin, an alkyd resin, heat-resistant polyamide, etc., for high functional use can be industrially and very easily produced. In the process of the present invention, the cost for purification can be decreased since no expensive purification step can be necessary, the amount of acetic acid for use can be decreased, and high-purity isophthalic acid can be obtained at high yields.

EXAMPLES

The present invention will be described further in detail below by reference to Examples, to which, however, the present invention shall not be limited.

EXAMPLE 1

A continuous oxidation reaction of m-xylene was carried out by the use of a first reactor made of pressure-resistant titanium, which was equipped with a stirring device, a reflux condenser and a heating device and had a raw material introducing port, an air introducing port, a gas discharging port and a liquid refluxing port, a second reactor made of pressure-resistant titanium, which was similarly equipped with a stirring device, a reflux condenser and a heating device and had an air introducing port, a gas discharging port, a liquid refluxing port, an inlet port for recharging a reaction product and an outlet port for drawing out a reaction product, and a crystallizer.

First Step

The first reactor was continuously charged, as a feed liquid, with m-xylene, cobalt acetate tetrahydrate, manganese acetate tetrahydrate, hydrobromic acid and acetic acid. The rate of charging m-xylene was 100 parts by weight, and based on this, the rates of charging the other components of the feed liquid were 0.561 part for cobalt acetate tetrahydrate, 1.656 parts for manganese acetate tetrahydrate, 1.117 parts for hydrobromic acid (47%), and 896.7 parts for acetic acid (water content 10%). (The catalyst concentration based on the solvent weight was as follows: cobalt=147 ppm, manganese=412 ppm, and bromine=576 ppm). m-Xylene was oxidized while air was blown into the first reactor. While keeping temperature inside the reactor at 200° C. and the pressure at 16.5 kg/cm$^2$ G, the feed amount of air was adjusted such that an oxidation discharge gas had an oxygen concentration of 5% by volume. In this case, the rate of feeding m-xylene was 0.17 kg/hour per liter of the solvent volume within the first reactor, the average residence time was about 30 minutes, and the concentration of the total of isophthalic acid and intermediates within the first reactor was 15.6%.

Second Step

The resultant oxidation reaction mixture obtained in the first reactor was recharged into the second reactor, and subjected to post oxidation with air at 195° C. under a pressure of 12 kg/cm$^2$ G for an average residence time of 50 minutes. The oxygen concentration in a discharge gas was maintained at 3% by volume. The amount of $CO_2+CO$ formed in this oxidation step and contained in the discharge gas (which is an index for oxidation of acetic acid) was 0.41 mole per mole of the raw material m-xylene.

The oxidation reaction mixture obtained by the post oxidation in the second reactor was transferred to the crystallizer at 100° C. to precipitate isophthalic acid crystals. Isophthalic acid was recovered by filtering the resultant slurry with washing it with acetic acid. The remaining mother liquor was concentrated by distillation with a distillation column, and acetic acid was recovered as follows. A column bottom liquid was continuously fed to a film evaporator (in which a heat medium having a temperature of 240° C. was circulating) for 6 hours while the flow amount of the heat medium was adjusted such that a concentrated liquid had a temperature of 230° C., whereby high-boiling substances in the residue could be well separated (total acetic acid content in a residue liquid in the film evaporator 4.3%). Acetic acid recovered from the distillation column and from the film evaporator was purified with a rectifying column, and used as a washing liquid in the next step.

Third Step

A suspension prepared by adding purified acetic acid (water content 10%) of the isophthalic acid crystals separated above (the amount of purified acetic acid was 1.5 times the weight of the isophthalic acid crystals) was transferred to a washing vessel, and kept at 150° C. for 30 minutes with stirring. The resultant suspension was cooled to 100° C. and filtered, and the resultant solid was dried to give 146 parts by weight, based on the m-xylene, of purified isophthalic acid having high purity and excellent whiteness. The yield of the isophthalic acid based on the raw material m-xylene was 93.0 mol.

EXAMPLE 2

In Example 1, the catalyst concentration was changed to 1.5 times, and an oxidation reaction was carried out at a temperature of 190° C. Post oxidation treatment was carried out in the same manner as in Example 1, and crystallization and washing treatment was carried out in the same manner as in Example 1. As a result, purified isophthalic acid having high purity and excellent whiteness was obtained. A filtrate mother liquor was treated with a distillation column and a film evaporator in the same manner as in Example 1, whereby acetic acid could be smoothly recovered (total acetic acid content in residue liquid in the film evaporator 5.5%).

COMPARATIVE EXAMPLE 1

In Example 2, an oxidation reaction in the first step was carried out at a temperature of 215° C. As a result, crude isophthalic acid obtained by post oxidation in the second step had a low 3CBA concentration. The filtrate mother liquor was subjected to acetic acid recovery with a film evaporator in the same manner as in Example 1 to show that the fluidity of the residue was poor and the film evaporator was not operable.

EXAMPLE 3

A first reactor was continuously charged, as a feed liquid, with m-xylene, cobalt acetate tetrahydrate, manganese acetate tetrahydrate, hydrobromic acid and acetic acid. The rate of charging m-xylene was 60 parts by weight, and based on this, the rates of charging the other components for the feed liquid were 0.561 part for cobalt acetate tetrahydrate, 1.656 parts for manganese acetate tetrahydrate, 1.551 parts for hydrobromic acid (47%), and 496.2 parts for acetic acid (water content 10%). (The catalyst concentration based on the solvent weight was as follows: cobalt=276 ppm, manganese=773 ppm, and bromine=1,500 ppm). m-Xylene was oxidized while air was blown into the first reactor. While keeping the temperature inside the reactor at 190° C. and the pressure at 16.5 kg/cm$^2$ G, the feed amount of air was adjusted such that an oxidation discharge gas had an oxygen concentration of 5% by volume. In this case, the rate of feeding m-xylene was 0.09 kg/hour per liter of the solvent volume within the first reactor, the average residence time was about 55 minutes, and the concentration of the total of isophthalic acid and intermediates within the first reactor was 19.0%.

The resultant oxidation reaction mixture obtained in the first reactor was recharged into a second reactor, and subjected to post oxidation with air at 185° C. under a pressure of 12 kg/cm$^2$ G for an average residence time of 50 minutes. The oxygen concentration in the discharge gas was maintained at 3% by volume.

Thereafter, the post oxidation reaction product was treated in the same manner as in Example 1 to give isophthalic acid having high purity and excellent whiteness. The filtrate mother liquor was treated with a distillation column and a film evaporator in the same manner as in Example 1, whereby acetic acid could be smoothly recovered (total acetic acid content in residue liquid in the film evaporator 5.0%).

COMPARATIVE EXAMPLE 2

Example 3 was repeated except that the rates of charging cobalt acetate tetrahydrate and manganese acetate tetrahydrate were changed to 1.795 parts and 0.442 parts (ratio of manganese to cobalt 0.25).

As a result, isophthalic acid crystals obtained by post oxidation in the second step had a low 3CBA concentration. The filtrate mother liquor was subjected to acetic acid recovery with a film evaporator in the same manner as in Example 1 to show that the fluidity of a residue was poor and the film evaporator was not operable.

COMPARATIVE EXAMPLE 3

The first step in Example 1 was repeated, and post oxidation in a second step was carried out at 165° C. under a pressure of 7 kg/cm$^2$ G. As a result, the filtrate mother liquor was smoothly treated with a distillation column and a film evaporator to recover acetic acid (total acetic acid content in residue liquid in the film evaporator 4.8%). However, purified isophthalic acid had a high 3CBA concentration and was colored.

COMPARATIVE EXAMPLE 4

Example 1 was repeated except that the washing temperature in the third step was changed to 90° C. As a result, coloring of purified isophthalic acid was observed.

Table 1 shows the main operational conditions and results of analysis of the isophthalic acid crystals obtained in Examples and Comparative Examples.

In addition, each crude isophthalic acid in Table 1 was obtained by directly recharging an oxidation reaction mixture from the first or second reactor into a pressure sample container, and separating a solid with washing it with acetic acid at 100° C.

3CBA and a resin color were measured as follows.

(1) 3CBA: determined by polarography. For high-purity isophthalic acid, the 3CBA concentration is required to be not more than 50 ppm.

(2) Resin color: Isophthalic acid, fumaric acid, neopentyl glycol and propylene glycol were polymerized in an isophthalic acid/fumaric acid/neopentyl glycol/propylene glycol molar ratio of 57/43/50/53, and the resultant resin was measured for a Hazen color number by dissolving it in styrene (resin content 60% by weight). A resin showing a smaller Hazen color number has a better resin color. For high-purity isophthalic acid, the Hazen color number is required to be not more than 30.

(3) m-Toluic acid: determined by gas chromatography of an esterified sample.

TABLE 1

| | Example/Comparative Example | | | | | | |
|---|---|---|---|---|---|---|---|
| | Ex. 1 | Ex. 2 | CEx. 1 | Ex. 3 | CEx. 2 | CEx. 3 | CEx. 4 |
| Feed amount of m-xylene, kg | 100 | 100 | 100 | 60 | 60 | 100 | 100 |
| Feed rate of m-xylene, kg/H/l | 0.17 | 0.17 | 0.17 | 0.09 | 0.09 | 0.17 | 0.17 |
| Acetic acid/m-xylene weight ratio | 9.0 | 9.0 | 9.0 | 8.0 | 8.0 | 9.0 | 9.0 |
| Cobalt (Co) concentration, ppm | 147 | 221 | 221 | 276 | 884 | 147 | 147 |
| Manganese (Mg) concentration, ppm | 412 | 618 | 618 | 773 | 206 | 412 | 412 |
| Bromine (Br) concentration, ppm | 576 | 866 | 866 | 1,500 | 1,500 | 576 | 576 |
| Mn/Co atomic ratio | 3.0 | 3.0 | 3.0 | 3.0 | 0.25 | 3.0 | 3.0 |
| Br/(Co + Mn) atomic ratio | 0.72 | 0.72 | 0.72 | 1.0 | 1.0 | 0.72 | 0.72 |
| Main oxidation temperature, °C. | 200 | 190 | 215 | 190 | 190 | 200 | 200 |
| Residence time, min. | 30 | 30 | 30 | 55 | 55 | 30 | 30 |
| Oxygen concentration in discharge gas, vol % | 5.0 | 5.0 | 5.0 | 5.0 | 5.0 | 5.0 | 5.0 |
| Post oxidation temperature, °C. | 195 | 185 | 195 | 185 | 185 | 165 | 195 |
| Amount of (CO + CO$_2$) formed, mol/mol | 0.41 | 0.35 | 0.59 | 0.50 | 0.65 | 0.39 | 0.41 |
| 2nd step, treatment with film evaporator | good | good | No | good | No | good | good |
| 3rd step, temperature for washing with acetic acid, °C. | 150 | 150 | 150 | 150 | 150 | 150 | 90 |
| 3CBA concentration, ppm | | | | | | | |
| Crude isophtahlic | 6,000 | 7,400 | 2,850 | 2,080 | 900 | 6,000 | 6,000 |

TABLE 1-continued

| | Ex. 1 | Ex. 2 | CEx. 1 | Ex. 3 | CEx. 2 | CEx. 3 | CEx. 4 |
|---|---|---|---|---|---|---|---|
| acid (after main oxidation) | | | | | | | |
| Crude isophthalic acid (after post oxidation) | 188 | 240 | 90 | 150 | 90 | 900 | 188 |
| Purified isophthalic acid | 34 | 44 | 16 | 27 | 16 | 164 | 34 |
| Resin color (purified isophthalic acid) | 30 | 20 | 50 | 30 | 40 | 60 | 40 |

What is claimed is:

1. A process for producing high-purity isophthalic acid by oxidizing m-xylene with an oxygen-containing gas in a solvent of hydrous acetic acid in the presence of a cobalt/manganese/bromine system catalyst, the process comprising:

a. a first step of feeding an oxidation reactor with the solvent, m-xylene of which the amount is 1 to 1/15 times the weight of the solvent and the catalyst in which the total amount of cobalt and manganese is in the range between 300 ppm and 1,500 ppm based on the weight of the solvent, the atomic ratio of manganese to cobalt is 0.5 to 5 and the atomic ratio of bromine to the total amount of cobalt and manganese is 0.5 to 1.5, the m-xylene being fed continuously, and carrying out oxidation of m-xylene at a temperature between 180° C. and 210° C. with maintaining 2 to 8% by volume of an oxygen concentration in a discharge gas until crude isophthalic acid produced in this first step has a 3-carboxybenzaldehyde concentration in the range between 500 ppm and 10,000 ppm and the total amount of isophthalic acid and intermediates produced by the oxidation is 10 to 35% by weight based on the weight of the solvent, b. a second step of further oxidizing a mixture formed by the oxidation in the first step until the crude isophthalic acid has a 3-carboxybenzaldehyde concentration in the range between 100 ppm and 800 ppm, separating the crude isophthalic acid, evaporating remaining mother liquor to obtain a condensate, and purifying the condensate by distillation to recover acetic acid, and c. a third step of mixing the crude isophthalic acid separated in the second step with purified acetic acid, treating the resultant mixture by stirring it at a temperature of not less than 100° C., and separating purified isophthalic acid.

2. A process according to claim 1, wherein the intermediates are m-toluic acid and 3-carboxybenzaldehyde.

3. A process according to claim 1, wherein the solvent of hydrous acetic acid contains 3 to 15% by weight of water and 85 to 97% by weight of acetic acid.

4. A process according to claim 1, wherein the amount of m-xylene is one third to one twelfth of the weight of the solvent.

5. A process according to claim 1, wherein the cobalt/manganese/bromine system catalyst contains carbonate, acetic acid salt tetrahydrate or bromide of cobalt.

6. A process according to claim 1, wherein the cobalt/manganese/bromine system catalyst contains carbonate, acetic acid salt tetrahydrate or bromide of manganese.

7. A process according to claim 1, wherein the cobalt/manganese/bromine system catalyst contains a bromine compound selected from the group consisting of hydrobromic acid, cobalt bromide and manganese bromide.

8. A process according to claim 1, wherein the total amount of cobalt and manganese based on the solvent weight is in the range between 400 ppm and 1,200 ppm.

9. A process according to claim 1, wherein the atomic ratio of manganese to cobalt is 0.8 to 4.

10. A process according to claim 1, wherein the atomic ratio of bromine to the total amount of cobalt and manganese is 0.6 to 1.2.

11. A process according to claim 1, wherein the mixture is oxidized in the second step at a temperature in the range between a temperature for the oxidation in the first step and a temperature which is lower than the temperature for the oxidation in the first step by about 30° C.

12. A process according to claim 12, wherein a discharge gas from the first step has an oxygen concentration of 3 to 6% by volume.

13. A process according to claim 12, wherein a discharge gas from the second step has an oxygen concentration of 2 to 7% by volume.

14. A process according to claim 1, wherein the second step further includes a step of subjecting the crude isophthalic acid to crystallization and precipitation and a step of separating the resultant isophthalic acid crystals by filtering.

15. A process according to claim 14, wherein the step of separating the isophthalic acid crystals by filtering further includes a step of evaporating mother liquor remaining after the isophthalic acid crystals have been separated to obtain a condensate and distilling the condensate to recover purified acetic acid.

16. A process according to claim 14, wherein the step of separating the isophthalic acid crystals by filtering further includes a step of feeding part of mother liquor remaining after the isophthalic acid crystals have been separated to the oxidation reactor in the first step.

17. A process according to claim 14, wherein the step of separating the isophthalic acid crystals by filtering further includes a step of subjecting mother liquor remaining after the isophthalic acid crystals have been separated to distillation and evaporating a column bottom liquid from said distillation to recover acetic acid from the resultant distillate and the resultant condensate.

18. A process according to claim 1, wherein the purified acetic acid in the third step is used in an amount which is 1 to 5 times the weight of the crude isophthalic acid.

19. A process according to claim 1, wherein acetic acid remaining after the purified isophthalic acid has been separated is used as a solvent in the first or second step.

* * * * *

UNITED STATES PATENT AND TRADEMARK OFFICE
CERTIFICATE OF CORRECTION

PATENT NO. : 5,132,450
DATED : July 21, 1992
INVENTOR(S) : KAZUO TANAKA, TERUMASA YOSHIDA, FUMIO OKOSHI, ICHIHEI MOTOYAMA, TAZUO OHTA and TOSHIAKI ABE It is certified that error appears in the above-identified patent and that said Letters Patent is hereby corrected as shown below:

Column 11, line 60, change "cobalt-" to read -- cobalt --;

line 63, change "cobalt-" to read -- cobalt --;

line 67, change "cobalt-" to read -- cobalt --.

Column 12, line 31, change "12" (second occurrence) to read -- 1 --.

Signed and Sealed this

Sixteenth Day of November, 1993

*Attest:*

BRUCE LEHMAN

*Attesting Officer*     *Commissioner of Patents and Trademarks*